United States Patent [19]

LeKhac

[11] Patent Number: 4,743,244

[45] Date of Patent: May 10, 1988

[54] WATER ABSORBING POLYMER COMPOSITIONS AND ARTICLES PREPARED THEREFROM

[75] Inventor: Bi LeKhac, West Chester, Pa.

[73] Assignee: Arco Chemical Company, Newtown Square, Pa.

[21] Appl. No.: 851,072

[22] Filed: Apr. 11, 1986

Related U.S. Application Data

[63] Continuation-in-part of Ser. No. 750,727, Jun. 28, 1985, abandoned.

[51] Int. Cl.$^4$ .................. A61F 13/16; C08L 71/00; C08L 71/02
[52] U.S. Cl. .................. 604/376; 128/156; 525/186; 525/187
[58] Field of Search .................. 604/372, 376, 367; 525/187, 186; 128/156

[56] References Cited

U.S. PATENT DOCUMENTS 3,387,061 6/1968 Smith et al. .................. 525/187
3,993,552 11/1976 Assarsson et al. .................. 525/187

OTHER PUBLICATIONS

Ikawa et al., *Journal of Polymer Science* (Polymer Chemistry Edition) vol. 3, No. 7, pp. 1505–1514 (Jul., 1975).

*Primary Examiner*—Allan M. Lieberman
*Attorney, Agent, or Firm*—Dennis M. Kozak

[57] ABSTRACT

A polymer composition which is water-absorbent upon curing comprising: (a) a copolymer containing from about 25 to about 75 mole percent recurring units of at least one $\alpha,\beta$-unsaturated monomer bearing at least one pendant unit selected from the group consisting of a carboxylic acid unit, a carboxylic acid salt unit, a carboxylic acid anhydride unit, a carboxylic acid imide unit, a carboxylic acid amide unit and a carboxylic acid ester unit and from about 75 to about 25 mole percent recurring units of a copolymerizable monomer; and, (b) a polyether derived from $C_2$ to $C_{10}$ alkylene oxides, wherein from about 20 to about 65 percent of the total pendant units introduced through the $\alpha,\beta$-unsaturated monomer must either be carboxylic acid units or must be converted to carboxylic acid units and from about 35 to about 80 percent of the pendant units must either be carboxylic acid salt units or must be converted to carboxylic acid salt units and wherein at least a portion of the oxide groups on the polyether are interacted with the carboxyl hydrogen atoms on the pendant carboxylic acid units such that the copolymer and the polyether are associated through hydrogen bonds.

17 Claims, No Drawings

WATER ABSORBING POLYMER COMPOSITIONS AND ARTICLES PREPARED THEREFROM

This application is a continuation-in-part of Ser. No. 750,727, filed on June 28, 1985, now abandoned.

This invention relates to water-absorbing resins.

In one of its more specific aspects, this invention relates to water swellable polymer compositions.

Water-absorbing resins are widely used in the manufacture of products which require high water absorption capability. For example water-absorbing resins are used in the manufacture of surgical and dental sponges, catamenial tampons, bandages, disposable diapers, meat trays, household pet litter, mats, etc. These resins are also used for the modification of soil to improve water retention and increase air capacity and for a host of other applications.

As used herein, the term "water" when used in the phrases "water-absorbing" and "water-absorbent" is understood to mean not only water but also electrolyte solutions such as body fluids.

A number of polymer compositions have been developed which exhibit improved stability and water and saline liquid absorption capacity. Thus, U.S. Pat. Nos. 3,954,721 and 3,983,095 disclose preparations for derivatives of copolymers of maleic anhydride with at least one suitable vinyl monomer in fiberous form. The fiberous copolymers are rendered hydrophilic and water-swellable by reaction with ammonia or an alkali metal hydroxide. U.S. Pat. No. 3,810,468 discloses lightly crosslinked olefin-maleic anhydride copolymers prepared as a substantially linear copolymers and then reacted with a diol or a diamine to introduce cross-linking. The resultant lightly crosslinked copolymers are treated with ammonia or an aqueous or alcoholic solution of an alkali metal hydroxide. U.S. Pat. No. 3,989,586 describes the preparation of sorbtive paper products by incorporating crosslinked copolymers of styrene or olefins with maleic anhydride in a paper web which is then treated to convert the copolymer to a water swellable salt form. U.S. Pat. No. 3,980,663 describes water swellable absorbent articles made from carboxylic polyelectrolytes via cross-linking with glycerine diglycidyl ether. U.S. Pat. Nos. 4,332,917 and 4,338,417 disclose blends of copolymers of styrene and maleic anhydride with polymers derived from a monomeric ester having vinyl unsaturation e.g. poly(vinyl acetate), cellulose triacetate, cellulose aceto-butyrate, poly(ethylacrylate) and poly(methylmethacrylate). U.S. Pat. No. 4,420,588 teaches a water-absorbing rubber composition comprising a 1,3-diene rubber and a water-absorbing resin dispersed in the rubber.

The water absorbing resins described in the above patents are all based on crosslinked copolymers prepared by introducing various amounts of crosslinking agents and, the resulting crosslinking reactions occur at temperatures as low as 100° C. Inasmuch as fiber formation e.g. fiber spinning cannot be achieved if any substantial degree of crosslinking has occurred, these prior art compositions are deficient in that they have no shelf life—fiber spinning must be carried out almost immediately after the crosslinking agent is introduced.

The water-absorbing polymer compositions of this invention possess excellent shelf life; they facilitate fiber formation over a much wider range of time and temperature. They also possess excellent integrity in the hydrogel or water swollen state, and exhibit excellent water and saline liquid absorption capacity.

According to this invention there is provided a polymer composition which is water-absorbent upon curing comprising: (a) a copolymer containing from about 25 to about 75 mole percent recurring units of at least one $\alpha,\beta$-unsaturated monomer bearing at least one pendant unit selected from the group consisting of a carboxylic acid unit, a carboxylic acid salt unit, a carboxylic acid anhydride unit, a carboxylic acid imide unit, a carboxylic acid amide unit and a carboxylic acid ester unit and from about 75 to about 25 mole percent and recurring units of a copolymerizable monomer; and, (b) a polyether derived from $C_2$ to $C_{10}$ alkylene oxides, wherein from about 20 to about 65 percent of the total pendant units introduced through the $\alpha,\beta$-unsaturated monomer must either be carboxylic acid units or must be converted to carboxylic acid units and from about 35 to about 80 percent of the pendant units must either be carboxylic acid salt units or must be converted to carboxylic acid salt units and wherein at least a portion of the oxide groups on the polyether are interacted with the carboxyl hydrogen atoms on the pendant carboxylic acid units such that the copolymer and the polyether are associated through hydrogen bonds.

Also, according to this invention there is provided a method of producing a water-absorbing polymer composition which comprises: (A) mixing a copolymer containing (i) from about 25 to about 75 mole percent recurring units of at least one $\alpha,\beta$-unsaturated monomer bearing at least one pendant unit selected from the group consisting of a carboxylic acid unit, a carboxylic acid salt unit, a carboxylic acid anhydride unit, a carboxylic acid imide unit, a carboxylic acid amide unit and a carboxylic acid ester and from about 75 to about 25 mole percent recurring units of a copolymerizable monomer; and, (ii) a polyether derived from $C_2$ to $C_{10}$ alkylene oxides, wherein from about 20 to about 65 percent of the total pendant units introduced through the $\alpha,\beta$-unsaturated monomer must either be carboxylic acid units or must be converted to carboxylic acid units and from about 35 to about 80 percent of the pendant units must either be carboxylic acid salt units or must be converted to carboxylic acid salt units and wherein at least a portion of the oxide groups on the polyether are interacted with the carboxyl hydrogen atoms on the pendant carboxylic acid units such that the copolymer and the polyether are associated through hydrogen bonds and, (B) curing the resulting polymer composition.

According to this invention there is also provided an article having excellent water and electrolytic solution absorption capacity comprising a cured water-absorbing polymer composition and a means for supporting said composition to present said composition for absorption usage, wherein said polymer composition comprises: (a) a copolymer containing from about 25 to about 75 mole percent recurring units of at least one $\alpha,\beta$-unsaturated monomer bearing at least one pendant unit selected from the group consisting of a carboxylic acid unit, a carboxylic acid salt unit, a carboxylic acid anhydride unit, a carboxylic acid imide unit, a carboxylic acid amide unit and a carboxylic acid ester unit and from about 75 to about 25 mole percent and recurring units of a copolymerizable monomer; and, (b) a polyether derived from $C_2$ to $C_{10}$ alkylene oxides, wherein from about 20 to about 65 percent of the total pendant units introduced through the $\alpha,\beta$-unsaturated monomer must either be carboxylic acid units or must be converted to carboxylic acid units and from about 35 to about 80 percent of the pendant units must either be carboxylic acid salt units or must be converted to carboxylic acid salt units and wherein at least a portion of the oxide groups on the polyether are interacted with the carboxyl hydrogen atoms on the pendant carboxylic acid units such that the copolymer and the polyether are associated through hydrogen bonds.

According to this invention there is also provided a method of enhancing the water and electrolyte solution absorption capacity of an article which method comprises incorporating into the article a water-absorbing polymer composition which comprises (a) a copolymer containing from about 25 to about 75 mole percent recurring units of at least one $\alpha,\beta$-unsaturated monomer bearing at least one pendant unit selected from the group consisting of a carboxylic acid unit, a carboxylic acid salt unit, a carboxylic acid anhydride unit, a carboxylic acid imide unit, a carboxylic acid amide unit and a carboxylic acid ester unit and from about 75 to about 25 mole percent and recurring units of a copolymerizable monomer; and, (b) a polyether derived from $C_2$ to $C_{10}$ alkylene oxides, wherein from about 20 to about 65 percent of the total pendant units introduced through the $\alpha,\beta$-unsaturated monomer must either be carboxylic acid units or must be converted to carboxylic acid units and from about 35 to about 80 percent of the pendant units must either be carboxylic acid salt units or must be converted to carboxylic acid salt units and wherein at least a portion of the oxide groups on the polyether are interacted with the carboxyl hydrogen atoms on the pendant carboxylic acid units such that the copolymer and the polyether are associated through hydrogen bonds; the polymer composition being incorporated into the article in an effective amount to enhance the water and saline liquid absorption capacity of the article as compared to the water and saline liquid absorption capacity of the article in the absence of the polymer composition.

As used herein, the term "hydrogen bond(s)" is understood to mean a non-bonded interaction between the hydrogen atoms on the recurring $\alpha,\beta$-unsaturated monomer units of the copolymer and the recurring oxide units of the polyether. More specifically, the non-bonded interaction occurs between the carboxyl acid hydrogen attached to the carboxyl acid oxygen and the alkylene oxide oxygen. Accordingly, the polymer compositions of this invention are complexed through hydrogen bonding and not covalent bonding. This is demonstrated in following Example 7, which demonstrates that a polymer composition of this invention is water-insoluble at ambient temperature and water soluble at elevated temperature.

Specially important to this invention are the pendant groups on the recurring units of the $\alpha,\beta$-unsaturated monomer. It has been found that both pendant carboxylic acid groups and pendant carboxylate salt groups are needed in the practice of this invention. And, the ratio of pendant carboxylic acid units to pendant carboxylate salt units is a significant determinant in the water-absorbing characteristics of the resultant water absorbing composition.

It has been found that the water-absorbing polymer compositions of this invention must contain a copolymer which contains in mole percent from about 25 to about 75 recurring units of the $\alpha,\beta$-unsaturated monomer bearing at least one pendant group. Moreover, it has been found that from about 35 to about 80 percent of the total pendant groups introduced into the copolymer through the $\alpha,\beta$-unsaturated monomer must be or must be convertible to carboxylate salt units with the balance being carboxylic acid units or being convertible to carboxylic acid units. If less than about 35 percent of the carboxylic acid units are neutralized, that is, less than 35 percent carboxylate salt units are introduced into the copolymer, the resultant composition exhibits poor water-absorbing characteristics. And, if more than 80 percent of the carboxylic acid units are neutralized, that is, more than 80 percent carboxylate salt units are introduced, there is insufficient hydrogen bonding to adequately tie the polymers together.

If the $\alpha,\beta$-unsaturated monomer selected for use in the practice of this invention contains only pendant carboxylic acid units, then from about 35 to about 80 percent of the carboxylic acid units must be neutralized by reaction with a strong organic or inorganic base such as NaOH, KOH, ammonia, ammonia-in-water solutions or organic amines. This modification reaction may be carried out before or after the polymers are mixed and may result in the formation of ion-dipole interactions which in addition to hydrogen bonds serve to complex the copolymer and the polyethers.

The phrase "a group convertible to a carboxyl group" is understood to mean and include carboxylic acid salt groups, carboxylic acid amide groups, carboxylic acid imide groups, carboxylic acid anhydride groups and carboxylic acid ester groups.

In the practice of this invention, 20 to 65 percent of the groups attached to the $\alpha,\beta$-unsaturated monomer need to have hydrogen atoms thereon. If the monomer bears only carboxylic acid amide, imide, anhydride or ester groups, hydrogen atoms can be formed thereon by a hydrolysis reaction. If the monomer bears only carboxylic acid salt groups, hydrogen atoms can be formed thereon by an acidification reaction. If the monomer bears only carboxyl groups, it already has hydrogen atoms thereon and then must be partially neutralized as described above. And, if the monomer contains both a carboxyl group and a group convertible to a carboxyl group, additional hydrogen atoms can be attached by carrying out one of the above-mentioned reactions.

The sequence and the number of reactions (hydrolysis, acidification, neutralization, etc.) carried out to give the desired functionality attached to the copolymer backbone are not critical. Any number and sequence resulting in a final copolymer which possesses from about 35 to about 80 percent pendant carboxylate salt units and from about 20 to about 65 percent pendant carboxylic acid units is suitable.

Representative $\alpha,\beta$-unsaturated monomers suitable for use in the practice of this invention include: maleic acid; crotonic acid; fumaric acid; mesaconic acid; the sodium salt of maleic acid; the sodium salt of 2-methyl, 2-butene dicarboxylic acid; the sodium salt of itaconic acid; maleamic acid; maleamide; N-phenyl maleimide; maleimide, maleic anhydride, fumaric anhydride, itaconic anhydride, citraconic anhydride, mesaconic anhydride, methyl itaconic anhydride, ethyl maleic anhydride; diethylmaleate; methylmaleate and the like, and their mixtures.

To form a copolymer suitable for use in this invention, the $\alpha,\beta$-unsaturated monomer is copolymerized with any suitable comonomer.

Suitable comonomers include for example: ethylene, propylene, isobutylene, $C_1$ to $C_4$ alkyl acrylates, $C_1$ to C₄ alkyl methacrylates, vinyl acetate, methyl vinyl ether and styrenic compounds having the formula:

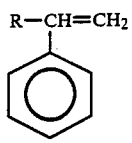

wherein R represents hydrogen or an alkyl group having from 1 to 6 carbon atoms and wherein the benzene ring may be substituted with low molecular weight alkyl or hydroxy groups.

The above-mentioned $C_1$ to $C_4$ alkyl acrylates include for example, methyl acrylate, ethyl acrylate, isopropyl acrylate, n-propyl acrylate, n-butyl acrylate, and the like, and their mixtures.

The above-mentioned $C_1$ to $C_4$ alkyl methyacrylates include for example methyl methacrylate, ethyl methacrylate, isopropyl methacrylate, n-propylmethylmethacrylate, n-butyl methacrylate, and the like, and their mixtures.

The above-mentioned styrenic compounds include, for example, styrene, α-methylstyrene, p-methylstyrene, t-butyl styrene, and the like, and their mixtures.

Copolymers suitable for use in the practice of this invention which contain recurring units of an α,β-unsaturated monomer and recurring units of a copolymerizable monomer will contain in mole percent from about 25 to about 75 recurring units of the α,β-unsaturated monomer. Preferably, the copolymer will be about an equimolar copolymer.

One copolymer particularly suitable for use is a copolymer of maleic anhydride and isobutylene.

Copolymers of isobutylene and maleic anhydride can be prepared using any suitable method, such as the procedure described in Example I. Such copolymers are also commercially available from Kuraray Isoprene Chemical Co. Ltd., Tokyo, Japan under the designation ISOBAM. ISOBAM copolymers are available in several grades which are differentiated by viscosity molecular weight: ISOBAM-10, 160,000 to 170,000; ISOBAM-06, 80,000 to 90,000; ISOBAM-04, 55,000 to 65,000; and ISOBAM-600, 6,000 to 10,000.

In the practice of this invention any suitable polyether derived from $C_2$ to $C_{10}$ alkylene oxides can be employed.

Suitable polyethers include: poly(ethylene oxide), poly(propylene oxide), poly(isobutylene oxide), poly(tetramethylene oxide), and random and block linear or branched polyether copolymers comprising recurring units of at least two monomers selected from the group consisting of ethylene oxide, propylene oxide, isobutylene oxide, and tetrahydrofuran.

Particularly suitable for use in the practice of this invention are the poly(ethylene oxides) designated POLYOX® Water Soluble Resins commercially available from Union Carbide Corporation, Specialty Chemicals and Plastics Division. One specific grade particularly suitable for use is designated POLYOX® WSR-205. POLYOX® WSR-205 has a number average molecular weight derived from rheological measurements of 600,000.

Particularly suitable for use in the practice of this invention are the poly(propylene oxides) designated PAREL® Elastomers commercially available from Hercules Incorporated. One specific grade particularly suitable for use in PAREL® 58 Elastomer. PAREL 58 Elastomer is a copolymer of propylene oxide and allyl glycidyl ether, The allyl glycidyl ether is a crosslinkable monomer.

Also suitable for use in the practice of this invention are PLURONIC® Polymers which are available from BASF Wyandotte, and are a series of related block polymers terminating in hydroxyl groups with average molecular weights from about 1,000 to greater than about 15,000. A preferred PLURONIC® Polymer is grade "F108" which is a polyoxypropylene-polyoxyethylene block copolymer having an average molecular weight of about 14,000.

The polymer composition of this invention will contain from about 20 to about 80 weight percent of the copolymer containing the α,β-unsaturated monomer and from about 80 to about 20 weight percent of the polyether. Preferably, each polymer is present in an amount within the range of from about 40 to about 60 weight percent.

The polymer composition of this invention can be prepared using any suitable blending method such as described in the following examples.

After the polymer composition is prepared it can be further processed into any desired form. For example, the polymer composition can be subjected to injection molding; blow molding; extrusion; vacuum forming; casting; spray drying; air-assisted spray drying; wet, dry or flash spinning; air attenuation, melt blowing (see e.g. the melt blowing method of U.S. Pat. No. 4,380,570), and the like. The selection of the process is typically dictated by the shape for form needed for end use. The desired shape or form may be that of: a molded article, a laminate, a sheet, an extrudate, granules, powder, film, filament, fibers, strands, yarns, woven fabrics, nonwoven mats, and the like.

The polymer compositions of this invention and in particular, fabricated articles into which the polymer compositions are incorporated are suitable for use in a wide range of absorptive functions. The fabricated articles into which the compositions are incorporated typically serve the function of supporting the polymer composition and presenting it in a form adapted for the end use. Means to support and present the composition for absorptive use include but are not meant to be limited to the following supports: bandages, surgical and dental sponges, catamenial tampons, sanitary napkins, disposable diapers, meat trays, pads for absorption of perspiration and the like.

For example, if it is desired to incorporate a water-absorbing polymer composition of this invention in a disposable diaper, conventional fabrication methods could be used to form a diaper composite having the following layers: an outer impermeable polyethylene film liner, a first cellulosic pulp layer superimposed on the film, a fibrous pulp or mat layer of a water-absorbing polymer composition of this invention followed by an optional second cellulosic pulp layer and an inner permeable polyethylene film liner. The polymer composition in fibrous form is particularly suitable for most applications in that it facilitates a large surface area for contact with the liquid to be absorbed.

The following examples serve to further demonstrate the invention.

EXAMPLE 1

This example demonstrates the preparation of an equimolar isobutylene/maleic anhydride copolymer following the teaching of U.S. Pat. No. 3,720,651, which is incorporated herein by reference thereto.

A solution of about 243 g. of maleic anhydride, about 1000 ml of ethyl acetate and about 332 ml of tertbutanol was prepared and introduced into a one-gallon stirred reactor at room temperature under a nitrogen atmosphere.

To initiate polymerization, about 200 g. isobutylene, and 2.4 g. Vazor 64 polymerization initiator (azoisobutyronitrile, E. I. du Pont) were charged into the reactor.

The polymerization reaction was conducted at 60° C. for about 7 hours, the excess isobutylene was vented off and the resultant copolymer isolated by filtering and drying for 3 hours at 80° C. About 370 g. of copolymer were recovered.

The recovered copolymer, an equimolar copolymer of isobutylene/maleic anhydride, was tested and found to have a glass transition temperature of 165° C. (by differential scanning calorimetry "DSC").

EXAMPLE 2

This example demonstrates the preparation of a water-absorbing polymer composition of this invention using the equimolar isobutylene/maleic anhydride copolymer of Example 1.

About 100 g. of the isobutylene/maleic anhydride copolymer and about 500 g. of demineralized water were added to a mixing vessel with stirring and heated to about 90° C. When the temperature of the mixture reached 90° C., 55 g. of KOH pellets (87.7% purity) were slowly added to the mixing vessel over a 2 hour period.

After the KOH addition was completed, the contents of the mixing vessel were stirred for about 2 hours after which the isobutylene/maleic anhydride copolymer was observed to be completely dissolved. The pH of the resulting solution was about 8.

The solution was allowed to cool to about 30° C. and then mixed with about 100 g. of a block copolymer of ethylene oxide and propylene oxide designated "PLURONIC® F-108" commercially available from BASF. Water in the resulting mixture was allowed to evaporate until a solids content of about 60-70% by weight was obtained.

The mixture, a thick aqueous solution, was subjected to dry spinning at room temperature to isolate the polymer composition in fibrous form.

The resulting fibrous mass (50/50 weight ratio of isobutylene/maleic anhydride-PLURONIC® F-108) was dried in a vacuum oven at 150° C. for about 1 hour and weighed to obtain its dry weight.

The dried fibrous mass was then immersed in brine water (0.9 wt % NaCl) for 10 minutes, the unabsorbed brine filtered off and the swollen mass allowed to sit on a paper towel for 30 seconds and then weighed to obtain its wet weight. The amount of brine absorbed was determined to be 4,470 weight percent based on the weight of the fibrous mass using the following formula:

$$\text{Brine Absorption (wt \%)} = \frac{\text{mass wet weight} - \text{mass dry weight}}{\text{mass dry weight}} \times 100$$

Three separate samples of the thick aqueous solution were subjected to heat aging prior to being fiberized by dry spinning. The three samples were found to be fiberizable after heat aging for: 30 days at 25° C., 2 days at 100° C. and 2 days at 120° C.

EXAMPLE 3

Using substantially the procedure of Example 2, two additional polymer compositions (A and B) were prepared and tested in brine (0.9 wt % NaCl). Polymer composition A was blended to provide an isobutylene/maleic anhydride copolymer to PLURONIC F-108 weight ratio of 67/33 and composition B to provide a weight ratio of 55/45. The fibrous mass of each composition was separately immersed in brine (0.9 wt % NaCl), for 10 minutes and recovered and tested to determine the amount of brine absorbed using the method described in Example 2.

Composition A (67/33) was found to absorb 3,020 wt % brine and composition B (55/45) 3,060 wt % brine.

EXAMPLE 4

Example 2 was repeated except that instead of using the isobutylene/maleic anhydride produced in Example 1, 100 g of ISOBAM-10, commercially available from Kuraray Isoprene Chemical Co. Ltd., was employed. The resulting fibrous mass was tested following the procedure in Example 2 and found to absorb 3,700 wt % brine.

Six fibrous samples prepared substantially according to the procedure of Example 2 using ISOBAM-10 were separately tested for brine (0.9 Wt % NaCl) absorption capacity at six different immersion periods within the range from 15 seconds to 11 minutes. The following Table shows the absorption results.

| Duration of immersion in brine | Brine Absorbed (wt %) |
| --- | --- |
| 15 sec. | 2,370 |
| 1 min. | 3,370 |
| 2 min. | 3,280 |
| 5 min. | 3,700 |
| 10 min. | 3,700 |
| 11 min. | 3,840 |

The data contained in the above Examples and Table serve to show that the polymer compositions of this invention exhibit excellent brine absorption capacity and speed.

EXAMPLE 5

This example demonstrates the preparation of a water-absorbing polymer composition of this invention using ISOBAM-10 copolymer and PAREL-58 Elastomer.

About 10 g of ISOBAM-10 (isobutylene/maleic anhydride) and about 100 g of demineralized water were added to a beaker with stirring and heated to about 90° C. When the temperature of the mixture reached 90° C., 5.5 g of KOH pellets (87.7% purity) were slowly added to the mixing beaker over a 2-hour period.

After the KOH addition was completed, the contents of the mixing beaker were stirred for about 2 hours after which the ISOBAM-10 copolymer was observed to be completely dissolved. The pH of the resulting solutuion was about 8.

The solution was allowed to cool to about room temperature and then poured into another beaker containing about 500 ml of cold methanol to precipitate the partially neutralized ISOBAM-10 copolymer into a thin paste. The methanol was then decanted leaving the paste of partially neutralized ISOBAM-10 copolymer in methanol.

In a separate beaker, about 3 g of PAREL-58 [poly(propylene oxide)] was previously dissolved in 100 ml of methanol at room temperature. To this solution, the paste of partially neutralized ISOBAM-10 copolymer was then added with mixing. Methanol in the resulting mixture was allowed to evaporate until a solids content of about 60-70% by weight was obtained.

The mixture, a thick solution, was subjected to dry spinning at room temperature to isolate the polymer composition in fibrous form.

The resulting fibrous mass (77/23 weight ratio of ISOBAM-10/PAREL-58) was dried in a vacuum oven at 150° C. for about 1 hour and weighed to obtain its dry weight. The amounts of brine (0.9 wt % NaCl) absorbed were determined to be 2,100, 2,600, and 2,800 weight percent for the durations of immersion in brine of 10, 30, and 60 minutes, respectively.

EXAMPLE 6

Example 2 was repeated except that instead of using PLURONIC-F108 copolymer, POLYOX WSR-205, a poly(ethylene oxide) commercially available from Union Carbide Corporation, was employed. The resulting fibrous mass was tested following the procedure in Example 2, and found to absorb 3,200 wt. % brine.

EXAMPLE 7

This example demonstrates that the polymer compositions of this invention are complexed through hydrogen bonds and not through covalent bonds.

A fibrous mass sample of a polymer composition of this invention was prepared using substantially the materials and procedure of Example 2 with the exception that the fibrous mass was dried in a vacuum oven at a drying temperature of 160° C. instead of 150° C. A 0.8203 g sample of the fibrous mass was subjected to Soxhlet extraction at the refluxing temperature of demineralized water for 24 hours. The extracted polymer was recovered by drying in a vacuum over at 130° C. for 16 hours. The amount of soluble polymer was found to be 0.7935 g or 96%. Moreover, there was no noticeable amount of insoluble polymer found on the cellulose extraction thimble.

It will be evident from the foregoing that various modifications can be made to this invention. Such, however, are considered as being within the scope of the invention.

What is claimed is:

1. A method of producing a shaped article having excellent water and electrolyte absorption capacity comprising the steps of
   (a) preparing a blend of (i) a copolymer containing from about 25 to about 75 mole percent recurring units of at least one $\alpha,\beta$-unsaturated monomer bearing at least one pendant unit selected from the group consisting of a carboxylic acid unit, a carboxylic acid sale unit, a carboxylic acid anhydride unit, a carboxylic acid imide unit, a carboxylic acid amide unit, and a carboxylic acid ester unit and from about 75 to about 25 mole percent recurring units of a copolymerizable monomer; and (ii) a polyether derived from $C_2$ to $C_{10}$ alkylene oxides, wherein from about 20 to about 65 percent of the total pendant units introduced through the $\alpha,\beta$-unsaturated monomer must either be carboxylic acid units or must be converted to carboxylic acid units and from about 35 to about 80 percent of the pendant units must either be carboxylic acid salt units or must be converted to carboxylic acid salt units and wherein at least a portion of the oxide groups on the polyether are interacted with the carboxyl hydrogen atoms on the pendant carboxylic acid units such that the copolymer and the polyether are associated through hydrogen bonds;
   (b) forming the resulting blend into a shaped article before it is fully cured; and
   (c) completing the cure of the blend in the form of said shaped article.

2. The method of claim 1 in which the blend is formed into fibers.

3. The method of claim 1 in which the blend is formed into powder.

4. The method of claim 1 in which the blend is formed into film.

5. The method of claim 1 in which said curing is induced by heating the blend.

6. The method of claim 1 in which said copolymer and said polyether are further associated through ion-dipole interactions.

7. An article of manufacture having excellent water and electrolyte absorption capacity comprising a cured water-absorbing polymer composition and a means for supporting said composition to present said composition for absorption usage, wherein said polymer composition comprises a blend of: (a) from about 20 to about 80 weight percent a copolymer containing from about 25 to about 75 mole percent recurring units of at least one $\alpha,\beta$-unsaturated monomer bearing at least one pendant unit selected from the group consisting of a carboxylic acid unit, a carboxylic acid salt unit, a carboxylic acid anhydride unit, a carboxylic acid imide unit, a carboxylic acid amide unit and a carboxylic acid ester unit and from about 75 to about 25 mole percent recurring units of a copolymerizable monomer; and, (b) from about 80 to about 20 weight percent a polyether derived from $C_2$ to $C_{10}$ alkylene oxides, wherein from about 20 to about 65 percent of the total pendant units introduced through the $\alpha,\beta$-unsaturated monomer must either be carboxylic acid units or must be converted to carboxylic acid units and from about 35 to about 80 percent of the pendant units must either be carboxylic acid salt units or must be converted to carboxylic acid salt units and wherein at least a portion of the oxide groups on the polyether are interacted with the carboxyl hydrogen atoms on the pendant carboxylic acid units such that the copolymer and the polyether are associated through hydrogen bonds.

8. The article of claim 7 in which said copolymer and said polyether are further associated through ion-dipole interactions.

9. The article of manufacture of claim 7 in which said support means is selected from the group consisting of bandages, surgical sponges, dental sponges, catamenial tampons, sanitary napkins, disposable diapers, and pads for absorption of perspiration.

10. The article of manufacture of claim 7 being a disposable diaper.

11. The article of manufacture of claim 8 being a disposable diaper.

12. A method of enhancing the water and electrolyte solution absorption capacity of an article which method comprises incorporating into the article a cured water-absorbing polymer composition which comprises a blend of: (a) from about 20 to about 80 weight percent a copolymer containing from about 25 to about 75 mole percent recurring units of at least one $\alpha,\beta$-unsaturated monomer bearing at least one pendant unit selected from the group consisting of a carboxylic acid unit, a carboxylic acid salt unit, a carboxylic acid anhydride unit, a carboxylic acid imide unit, a carboxylic acid amide unit and a carboxylic acid ester unit and from about 75 to about 25 mole percent recurring units of a copolymerizable monomer; and, (b) from about 80 to about 20 weight percent a polyether derived from $C_2$ to $C_{10}$ alkylene oxides, wherein from about 20 to about 65 percent of the total pendant units introduced through the $\alpha,\beta$-unsaturated monomer must either be carboxylic acid units or must be converted to carboxylic acid units and from about 35 to about 80 percent of the pendant units must either be carboxylic acid salt units or must be converted to carboxylic acid salt units and wherein at least a portion of the oxide groups on the polyether are interacted with the carboxyl hydrogen atoms on the pendant carboxylic acid units such that the copolymer and the polyether are associated through hydrogen bonds; the polymer composition being incorporated into the article in an effective amount to enhance the water and electrolyte absorption capacity of the article as compared to the water and electrolyte absorption capacity of the article in the absence of the polymer composition.

13. The method of claim 12 in which said copolymer and said polyether are further associated through ion-dipole interactions.

14. The method of claim 12 in which said polymer composition is incorporated in fibrous form.

15. The method of claim 13 in which said polymer composition is incorporated in fibrous form.

16. The method of claim 12 in which said article is a disposable diaper.

17. A method of absorbing water and electrolyte solutions comprising the step of contacting the water or electrolyte solution to be absorbed with a cured water-absorbing composition comprising a blend of: (a) from about 20 to about 80 weight percent a copolymer containing from about 25 to about 75 mole percent recurring units of at least one $\alpha,\beta$-unsaturated monomer bearing at least one pendant unit selected from the group consisting of a carboxylic acid unit, a carboxylic acid salt unit, a carboxylic acid anhydride unit, a carboxylic acid imide unit, a carboxylic acid amide unit and a carboxylic acid ester unit and from about 75 to about 25 mole percent recurring units of a copolymerizable monomer; and, (b) from about 80 to about 20 weight percent a polyether derived from $C_2$ to $C_{10}$ alkylene oxides, wherein from about 20 to about 65 percent of the total pendant units introduced through the $\alpha,\beta$-unsaturated monomer must either be carboxylic acid units or must be converted to carboxylic acid units and from about 35 to about 80 percent of the pendant units must either be carboxylic acid salt units or must be converted to carboxylic acid salt units and wherein at least a portion of the oxide groups on the polyether are interacted with the carboxyl hydrogen atoms on the pendant carboxylic acid units such that the copolymer and the polyether are associated through hydrogen bonds.

* * * * *